US008058472B2

(12) United States Patent
Pombeiro et al.

(10) Patent No.: US 8,058,472 B2

(45) Date of Patent: Nov. 15, 2011

(54) METHOD FOR THE CONVERSION, UNDER MILD CONDITIONS AND IN AQUEOUS MEDIUM, OF GASEOUS AND LIQUID ALKANES INTO CARBOXYLIC ACIDS

(75) Inventors: Armando Pombeiro, Lisbon (PT); Marina Kirillova, Lisbon (PT); Alexander Kirillov, Lisbon (PT); Jose Armando Silva, Lisbon (PT); Joao Frausto Da Silva, Lisbon (PT)

(73) Assignee: Instituto Superior Tecnico, Lisbon (PT)

( * ) Notice: Subject to any disclaimer, the term of this patent is extended or adjusted under 35 U.S.C. 154(b) by 127 days.

(21) Appl. No.: 12/523,757

(22) PCT Filed: Jan. 17, 2008

(86) PCT No.: PCT/PT2008/000003

§ 371 (c)(1), (2), (4) Date: Jul. 20, 2009

(87) PCT Pub. No.: WO2008/088234

PCT Pub. Date: Jul. 24, 2008

(65) Prior Publication Data

US 2010/0099912 A1 Apr. 22, 2010

(30) Foreign Application Priority Data

Jan. 18, 2007 (PT) ........................................ 103640

(51) Int. Cl.
*C07C 51/14* (2006.01)

(52) U.S. Cl. ..... 562/522; 562/400; 562/497; 562/512.4; 562/517; 562/521

(58) Field of Classification Search ........................ None
See application file for complete search history.

(56) References Cited

U.S. PATENT DOCUMENTS 5,281,752 A * 1/1994 Fujiwara et al. .............. 562/522

OTHER PUBLICATIONS

Search Report for International Patent Application No. PCT/PT2008/000003 dated May 26, 2008.

Reis et al: "Vanadium-catalyzed carboxylation of linear and cyclic C5 and C6 alkanes", Journal of Catalysis, vol. 235, pp. 333-340, XP002479064, Sep. 4, 2005.

Nizova GV et al: "Carboxylation of methane with CO or CO2 in aqueous solution catalysed by vanadium complexes", Chemical Communications—Chemcom, Royal Society of Chemistry, No. 17, pp. 1885-1886, XP002286129, Jan. 1, 1998.

Asadullah M et al: "One step carboxylation reaction of saturated hydrocarbons with CO by Co(OAc)2 catalyst under mild conditions", Applied Catalysis A: General, Elsevier Science, Amsterdam, NL, vol. 194-195, pp. 443-452, XP004272248, Mar. 13, 2000.

Reis P M et al: "Single-Pot Conversion of Methane into Acetic Acid in the Absence of CO and with Vanadium Catalysts Such as Amavadine", Angewandte Chemie. International Edition, Wiley VCH Verlag, Weinheim, vol. 42, No. 7, pp. 821-823, XP002286136, Feb. 17, 2003.

* cited by examiner

*Primary Examiner* — Sudhakar Katakam

(74) *Attorney, Agent, or Firm* — Pearl Cohen Zedek Latzer, LLP

(57) ABSTRACT

The present invention concerns a new efficient method for the selective transformation, under mild conditions and in aqueous medium, of gaseous (ethane, propane and n-butane) and liquid (n-pentane, n-hexane, cyclopentane and cyclohexane) alkanes into carboxylic acids bearing one more carbon atom, characterized by a single-pot low-temperature (25-60° C.) reaction of the alkane with carbon monoxide in water/acetonitrile liquid medium, either in the absence or in the presence of a metal catalyst, in systems containing also an oxidant (a peroxodisulphate salt).

FORMULA (I)

$$\geq C-H \xrightarrow[\text{H}_2\text{O/MeCN, 25-60° C. (catalyst)}]{\text{CO, } S_2O_8^{2-}} \geq C-COOH$$

11 Claims, No Drawings

METHOD FOR THE CONVERSION, UNDER MILD CONDITIONS AND IN AQUEOUS MEDIUM, OF GASEOUS AND LIQUID ALKANES INTO CARBOXYLIC ACIDS

CROSS-REFERENCE TO RELATED APPLICATIONS

This application is a National Phase Application of PCT International Application No. PCT/PT2008/000003, International Filing Date Jan. 17, 2008, claiming priority of Portuguese Patent Application No. 103640, filed Jan. 18, 2007, which is hereby incorporated by reference.

FIELD OF THE INVENTION

This invention relates to Organic Chemistry, Catalysis and Coordination Chemistry and concerns an efficient single-pot method for producing carboxylic acids from various alkanes via their low-temperature reaction with CO in $H_2O$/MeCN medium and in the presence of oxidant, either in metal-catalysed or in metal-free processes.

BACKGROUND OF THE INVENTION

In pursuit of recent studies carried out in our Laboratory on the carboxylation of alkanes to carboxylic acids in systems containing trifluoroacetic acid (TFA) as solvent, and various V and Re compounds as catalysts,[1,2] we have been searching for new more efficient methods to perform such a type of alkane transformations, aiming at the replacement of the considerably expensive, consumable in the reaction and corrosive TFA by another solvent or solvent composition, which could overcome the abovementioned drawbacks. Taking into consideration that the metal-catalysed peroxidative oxidation (namely with $H_2O_2$) of cycloalkanes to the corresponding alcohols and ketones can occur in water/acetonitrile liquid medium, as shown by other studies on alkane transformations performed e.g. in our Laboratory,[3,4] we have now found, for the first time, that this mixture of solvents can be also notably suitable for the efficient carboxylation by CO of both gaseous and liquid $C_n$ alkanes to give selectively carboxylic acids having (n+1) carbon atoms even in the absence of a metal catalyst.

The present work has been developed at the Centro de Química Estrutural, Complexo I, Instituto Superior Técnico, Universidade Técnica de Lisboa, within the Ph.D. courses of Dr. M. V. Kirillova and Dr. A. M. Kirillov, as part of projects under the responsibility of Professor A. J. L Pombeiro, supported by the POCI-2010 programme (FEDER funded) of the Foundation for Science and Technology (FCT), and the European network (Human Resources and Mobility Marie-Curie Research Training Network, AQUACHEM project).

DETAILED DESCRIPTION OF THE INVENTION

(a) Objectives and Advantages

The $C_3$-$C_7$ aliphatic carboxylic acids are large-tonnage products of high importance in view of their wide industrial use.[5] Although various methods are known and currently applied for the production of these acids,[5] usually they require the use of considerably expensive raw materials and catalysts, several reaction stages and harsh reaction conditions, and exhibit low yields and selectivities.

Hence, the general aim of the current invention consists in finding a new improved method for the synthesis of those carboxylic acids which would not present the above limitations based on the use of alkanes (as abundant and relatively cheap raw materials), operating under mild conditions and using a convenient solvent composition, preferably containing water (aqueous medium).

A somehow related method, known before this invention, for alkane transformations, under moderate conditions, to carboxylic acids was initially developed by Fujiwara[6] and further optimized and extended to various alkanes and catalysts in our Laboratory.[1,2] This system is based on reacting an alkane with CO and a peroxodisulphate salt, at 80° C. in absolute trifluoroacetic acid (TFA) as solvent, and in the presence of a metal catalyst. The reaction failed when TFA was replaced by another solvent or when using a solvent composition comprising TFA and any other solvent (even in a low relative amount of the latter, e.g. 1:20). The use of $CO_2$, instead of CO, as the carbonylating agent[7] for the conversion of methane into acetic acid, also requires TFA as the adequate solvent. The use of TFA as solvent constitutes a strong drawback due to its high cost, difficult recovery and consumption along the reaction. Besides, TFA is a strong and highly corrosive acid and an environmentally intolerable solvent.

Hence, the principal advantages of the present invention are the following ones:

The use of a solvent (water/acetonitrile) that is simple, easily available and recyclable, inert under the reaction conditions applied, much cheaper than TFA and without the aggressiveness of this acid;

An operation under milder reaction conditions (50-60° C. vs. 80° C. in the method with TFA);

An easier separation of the products (carboxylic acids) from the reaction mixture, e.g. by extraction;

The possibility to perform the reactions without the use of any metal catalyst, in contrast to the TFA operating method which always requires a metal catalyst;

Superior selectivity, namely without formation of fluorinated by-products (e.g. trifluoroalkanes, trifluorocarboxylate esters and various alkyltriflates), typically obtained in the TFA containing method.

It is necessary to mention that although alkane transformations to carboxylic acids either in water or acetonitrile have already been studied,[8-10] they involve methods and systems that are different from those of the present invention, they exhibit very low activities (conversions of alkanes to carboxylic acids, based on alkane, usually do not exceed 3%), modest selectivities and restricted applications to particular alkanes.

Thus, further advantages of the current invention consist on the remarkably higher yields of carboxylic acids (up to 72% based on the alkane in a single batch), superior selectivities (which can also be controlled by the type of catalyst or its absence) and applicability to transform both $C_2$-$C_4$ gaseous and $C_5$-$C_6$ liquid linear or cyclic alkanes, or mixtures thereof. Moreover, it also exhibits a high oxidant efficiency (the product yield based on the oxidant is up to 48%).

Yet another particular advantage of the present invention comprises the possible use of a broad spectrum of transition metal (typically Cu, Fe, V, Mn or Cr) compounds, which include simple salts, oxides or various coordination compounds.

(b) Innovatory Features

The invention concerns a novel efficient method for the transformation, under mild conditions, of gaseous (ethane, propane and n-butane) and liquid (n-pentane, n-hexane, cyclopentane and cyclohexane) alkanes to carboxylic acids having one further carbon atom, by reacting at least one of the said alkanes with CO and a peroxodisulphate salt, in water/acetonitrile solvent, either in the absence or in the presence of a metal catalyst.

As it was indicated above, the carboxylation of alkanes by CO to carboxylic acids had already been achieved but, before this invention, the use of a strong acidic medium (as absolute trifluoroacetic acid) and the presence of a metal catalyst[1,2,6] were required in order to display an appreciable efficiency. Thus, the principal innovatory feature of the present invention consists in discovering a new solvent composition (i.e. water/acetonitrile mixture) that allows to transform various alkanes to carboxylic acids having one more carbon atom, in high yields and selectivities. This method shows various advantages, as mentioned above, and is economically attractive.

It should also be mentioned that the presence of the two solvents is essential, since the reaction does not proceed, under our reaction conditions, either in only water or acetonitrile. The water/acetonitrile mixture is particularly suitable and has never been applied for such a type of processes, although various solvents (e.g. TFA,[1,2,6] $H_2SO_4$,[7] $H_2O$,[8a,c,10b] $H_2O$/perfluorinated acid,[8b] etc.) have been tested for carboxylation of alkanes (with very low efficiencies apart from the TFA system).

Another important innovatory feature of the current invention concerns the possibility of performing the alkane carboxylation without the need for any metal catalyst, in contrast to what is required for most of the other processes for the formation of carboxylic acids. However, the reaction, in our method, may be accelerated by the presence of a metal catalyst, leading to higher conversions in shorter reaction times. We have discovered that copper compounds with triethanolamine are particularly adequate catalysts, namely the water-soluble tetranuclear complex $[O\subset Cu_4\{N(CH_2CH_2O)_3\}_4(BOH)_4][BF_4]_2$ which is known to catalyze the peroxidative oxidation of alkanes[3a,b,4a] but had never been applied for their carboxylation reactions.

Moreover, the current invention provides a rare process of C—C bond formation from gaseous and liquid alkanes which proceeds efficiently and selectively under mild conditions (temperature range of 25-60° C.) and in aqueous medium, displaying some considerable advantages not only over the known industrial processes for $C_3$-$C_7$ aliphatic carboxylic acids,[5] but also over the majority of alkane functionalization reactions.

(c) Technical Description

The invention concerns a new efficient method for the selective and single-pot transformation, under mild conditions, of various $C_n$ alkanes into carboxylic acids having (n+1) carbon atoms (Scheme 1), by allowing to react a mixture comprising an alkane, carbon monoxide, a peroxodisulphate salt as the oxidant and a catalyst (optional), in water/acetonitrile mixed solvent, preferably at 50-60° C. Thus, ethane can be directly transformed to propionic acid, propane to isobutyric and butyric acids, n-butane to 2-methylbutanoic acid, cyclopentane to cyclopentanecarboxylic acid, n-hexane to 2-methylhexanoic and 2-ethylpentanoic acids and cyclohexane to cyclohexanecarboxylic acid, respectively.

Scheme 1.

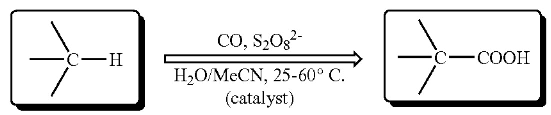

A detailed description of typical experimental procedures and a discussion of selected examples for alkane transformations according to this invention are given below.

1—Experimental Details

In a typical experiment the reaction mixtures were prepared as follows. To a 13.0 mL stainless steel autoclave, equipped with a Teflon-coated magnetic stirring bar, were added 0-32.0 μmol (typically 8.0 μmol) of catalyst (optional), 1.00-2.00 mmol (typically 1.50 mmol) of $K_2S_2O_8$, 2.0-3.0 mL of $H_2O$, 2.0-4.0 mL of MeCN and 1.00-1.50 mmol (typically 1.00 mmol) of liquid alkane (in the case of pentane, cyclopentane, hexane and cyclohexane). Then the autoclave was closed and flushed with dinitrogen three times for removing the air and pressurized with 20-40 atm (typically 20 atm) of carbon monoxide. In the case of using a gaseous alkane (ethane, propane or n-butane), the reactor had been pressurized with 1-10 atm of this gas prior to the admission of CO. The reaction mixture was vigorously stirred for 2-6 h at 25-60° C. using a magnetic stirrer and an oil bath, whereupon it was cooled in an ice bath, degassed, opened and transferred to a Schlenk tube. Diethyl ether (9.0-11.0 mL), to separate from the inorganic compounds, and cycloheptanone (90 μL, internal standard) were added. The obtained mixture was vigorously stirred and the organic layer was analyzed by gas chromatography (internal standard method) using a Fisons Instruments GC 8000 series gas chromatograph with a DB WAX fused silica capillary column (P/N 123-7032) and the Jasco-Borwin v. 1.50 software. In some cases, the products were also identified by GC-MS, $^1H$ and $^{13}C$-$\{^1H\}$ NMR techniques, using a Trio 2000 Fisons spectrometer with a coupled Carlo Erba (Auto/HRGC/MS) gas chromatograph, and a Varian UNITY 300 NMR spectrometer, respectively. The catalysts have been obtained either according to the previously described methods[3a,4a,12] or from commercial sources.

Examples of effects on the alkane carboxylation of various factors, such as the relative amounts of alkane, carbon monoxide, oxidant, solvent and its composition, catalyst type and reaction temperature, are listed in Tables 1 and 2 and discussed below.

2—Examples

Various alkanes can be carboxylated by CO in $H_2O$/MeCN medium to give carboxylic acids even in the absence of a metal catalyst (Table 1). The highest alkane conversions are observed for propane and n-pentane leading to total yields of $C_4$ and $C_6$ carboxylic acids up to ca. 34 and 18%, respectively (examples 2 and 4). In the other cases, the overall yields of carboxylic acids are in the 6-12% range.

TABLE 1

| Metal-free carboxylation of alkanes to the corresponding carboxylic acids in $H_2O$/MeCN medium.[a] | | | |
|---|---|---|---|
| Example | Alkane | Carboxylic acid (yield)[b] | Total yield, % |
| 1[c] | ethane | propionic (9.9%) | 9.9 |
| 2[d] | propane | isobutyric (29.8%), butyric acid (4.6%) | 34.4 |
| 3 | n-butane | 2-methylbutanoic (6.2%) | 6.2 |
| 4[e] | n-pentane | 2-methylpentanoic (4.2%), 2-ethylbutanoic (13.4%) | 17.6 |
| 5[f,g] | cyclopentane | cyclopentanecarboxylic (8.2%) | 8.2 |
| 6[e] | n-hexane | 2-methylhexanoic (4.5%), 2-ethylpentanoic (4.5%) | 9.0 |
| 7[g] | cyclohexane | cyclohexanecarboxylic (12.3%) | 12.3 |

[a]Selected results; typical (unless otherwise stated) reaction conditions: p(gaseous alkane) = 10, 5 or 1.5 atm (2.66, 1.33 or 0.40 mmol) for $C_2H_6$, $C_3H_8$ and n-$C_4H_{10}$, respectively; liquid alkane (1.00 mmol); p(CO) = 20 atm (5.32 mmol); $K_2S_2O_8$ (1.50 mmol); $H_2O$ (3.0 mL)/MeCN (3.0 mL); 60° C.; 6 h in an autoclave (13.0 mL capacity).

[b]Product yield % (moles of product/100 moles of alkane).

[c]$K_2S_2O_8$ (2.00 mmol).

[d]p(CO) = 30 atm.

[e]$H_2O$ (2.0 mL)/MeCN (4.0 mL).

[f]Cyclopentane (1.50 mmol).

[g]50° C.

The carboxylation of alkanes typically proceeds more efficiently in the presence of a metal catalyst, thus leading to higher yields of carboxylic acids which can usually be achieved in a shorter reaction time and at lower reaction temperature, in comparison with the same reaction performed in the absence of catalyst.

The tetracopper triethanolaminate complex $[O\subset Cu_4\{N(CH_2CH_2O)_3\}_4(BOH)_4][BF_4]_2$ exhibits the highest level of activity among the tested catalysts (Table 2). For this catalyst, the maximum overall yields for the various alkanes are in the following order: cyclohexanecarboxylic acid from cyclohexane (ca. 72%, example 15), 2-methylhexanoic and 2-ethylpentanoic acids from n-hexane (ca. 45%, example 14), isobutyric and butyric acids from propane (ca. 38%, example 9), 2-methylbutanoic acid from n-butane (ca. 30%, example 10), 2-methylpentanoic and 2-ethylbutanoic acids from n-pentane (ca. 23%, example 11), cyclopentanecarboxylic acid from cyclopentane (ca. 22%, example 12), and propionic acid from ethane (ca. 9%, example 8). The yields based on the peroxodisulphate oxidant are also high, being typically ⅔ of those based on alkane.

TABLE 2

| Metal-catalysed carboxylation of alkanes to the corresponding carboxylic acids in $H_2O$/MeCN medium.[a] | | | | |
|---|---|---|---|---|
| Example | Alkane | Catalyst | Total yield %[b] | Total TON[c] |
| 8[d] | ethane | $[O\subset Cu_4\{N(CH_2CH_2O)_3\}_4(BOH)_4][BF_4]_2$ | 9.4 | 30 |
| 9[d,e] | propane | $[O\subset Cu_4\{N(CH_2CH_2O)_3\}_4(BOH)_4][BF_4]_2$ | 38.0 | 37 |
| 10[f] | n-butane | $[O\subset Cu_4\{N(CH_2CH_2O)_3\}_4(BOH)_4][BF_4]_2$ | 29.6 | 15 |
| 11[e] | n-pentane | $[O\subset Cu_4\{N(CH_2CH_2O)_3\}_4(BOH)_4][BF_4]_2$ | 23.2 | 29 |
| 12[f,g,h] | cyclopentane | $[O\subset Cu_4\{N(CH_2CH_2O)_3\}_4(BOH)_4][BF_4]_2$ | 22.2 | 42 |
| 13[f,i] | cyclopentane | $[O\subset Cu_4\{N(CH_2CH_2O)_3\}_4(BOH)_4][BF_4]_2$ | 20.5 | 153 |
| 14[e] | n-hexane | $[O\subset Cu_4\{N(CH_2CH_2O)_3\}_4(BOH)_4][BF_4]_2$ | 44.6 | 56 |
| 15[f,j] | cyclohexane | $[O\subset Cu_4\{N(CH_2CH_2O)_3\}_4(BOH)_4][BF_4]_2$ | 72.3 | 181 |
| 16[f,i] | cyclohexane | $[O\subset Cu_4\{N(CH_2CH_2O)_3\}_4(BOH)_4][BF_4]_2$ | 50.4 | 252 |
| 17[f] | cyclohexane | $[Cu_2(H_2tea)_2\{C_6H_4(COO)_2\text{-}1,4\}]_n\cdot 2nH_2O$[l] | 38.8 | 49 |
| 18[f,m] | cyclohexane | $[Cu(H_2tea)(N_3)]$[l] | 32.5 | 41 |
| 19[f,n] | cyclohexane | $Cu(NO_3)_2\cdot 2.5H_2O$ | 31.6 | 10 |
| 20[f,o,p] | cyclohexane | $Ca[V\{ON(CH_2COO)_2\}_2]$ | 14.7 | 21 |
| 21[f,n] | cyclohexane | $K_2Cr_2O_7$ | 33.1 | 10 |

TABLE 2-continued

| Metal-catalysed carboxylation of alkanes to the corresponding carboxylic acids in $H_2O$/MeCN medium.[a] | | | | |
|---|---|---|---|---|
| Example | Alkane | Catalyst | Total yield %[b] | Total TON[c] |
| 22[f,n] | cyclohexane | $MnO_2$ | 14.4 | 4 |
| 23[f,m] | cyclohexane | $Fe(OH)_3$•$0.5H_2O$ | 15.8 | 10 |

[a]Selected results; typical (unless otherwise stated) reaction conditions: p(gaseous alkane) = 10, 3 or 1.5 atm (2.66, 0.78 or 0.40 mmol) for $C_2H_6$, $C_3H_8$ and n-$C_4H_{10}$, respectively; liquid alkane (1.00 mmol); p(CO) = 20 atm (5.32 mmol); catalyst (8.0 μmol); $K_2S_2O_8$ (1.50 mmol); $H_2O$ (3.0 mL)/MeCN (3.0 mL); 60° C.; 6 h in an autoclave (13.0 mL capacity).
[b]Product yield % (moles of product/100 moles of alkane); product yield based on oxidant can be estimated as [(yield based on alkane)/1.5].
[c]Moles of carboxylic acid products/mol of catalyst.
[d]p(CO) = 30 atm.
[e]$H_2O$ (2.0 mL)/MeCN (4.0 mL).
[f]50° C.
[g]cyclopentane (1.50 mmol).
[h]p(CO) = 40 atm.
[i]Catalyst (2.0 μmol).
[j]Catalyst (4.0 μmol).
[l]$H_2$tea = monodeprotonated form of triethanolamine.
[m]Catalyst (16.0 μmol).
[n]Catalyst (32.0/mol).
[o]$H_2O$ (2.0 mL)/MeCN (2.0 mL).
[p]Catalyst (10.0 μmol).

Other catalysts, namely $[Cu_2(H_2tea)_2\{C_6H_4(COO)_2\text{-}1,4\}]_n.2nH_2O$, $[Cu(H_2tea)(N_3)]$, $Cu(NO_3)_2.2.5H_2O$, $Ca[V\{ON(CH_2COO)_2\}_2]$, $K_2Cr_2O_7$, $MnO_2$ and $Fe(OH)_3.0.5H_2O$, can also be applied for the carboxylation of e.g. cyclohexane leading to yields of cyclohexanecarboxylic acid in the 14-39% range (Table 2, examples 17-23).

The catalyst amount has only a slight effect on the product yield, but lower catalyst amounts lead to quite higher TONs. For example, in the case of cyclopentane carboxylation, a catalyst amount decrease from 8.0 to 2.0 μmol leads only to a slight yield lowering from 22.2 to 20.5%, whereas the TON increases from 42 to 153 (Table 2, examples 12 and 13).

In both metal-free and metal-catalysed processes the secondary carbon atom in alkanes is more easily carboxylated favouring the formation of branched carboxylic acids. Moreover, the partial oxidation of linear alkanes to carboxylic acids (typically occurring in TFA containing systems) or to alcohols and ketones does not proceed, to a considerable extent, in our processes.

The efficiency of both metal-free and metal-catalysed processes for alkane carboxylation is dependent on various factors, namely the amount and composition of solvent mixture (the 1:1 or 1:2 $H_2O$/MeCN volumetric ratio usually is very favourable but not an exclusive one), and the CO pressure (the highest yields and selectivities are commonly achieved for the typical CO pressure of 20 atm). Nevertheless, other factors such as the type and amount of catalyst, oxidant amount, relative amounts of all the reaction components and reaction time, also influence the obtained results.

REFERENCES

[1] (a) P. M. Reis, J. A. L. Silva, A. F. Palavra, J. J. R. F. da Silva, T. Kitamura, Y. Fujiwara, A. J. L. Pombeiro, *Angew. Chem., Int. Ed.* 2003, 42, 821; (b) P. M. Reis, J. A. L. Silva, A. F. Palavra, J. J. R. F. da Silva, A. J. L. Pombeiro, *J. Catal.* 2005, 235, 333; (c) A. M. Kirillov, M. Haukka, M. V. Kirillova, A. J. L. Pombeiro, *Adv. Synth. Catal.* 2005, 347, 1435.

[2] (a) A. J. L. Pombeiro, J. J. R. Fraústo da Silva, Y. Fujiwara, J. A. L. Silva, P. M. Reis, A. F. Palavra, Patent WO 2004037416, 2004; (b) A. J. L. Pombeiro, J. J. R. Fraústo da Silva, J. A. L. Silva, M. V. Kirillova, P. M. Reis, A. F. Palavra, Y. Fujiwara, Patent PT 103131, 2004; (c) A. J. L. Pombeiro, M. V. Kirillova, A. M. Kirillov, J. J. R. Fraústo da Silva, Patent PT 103345, 2005; (d) A. J. L. Pombeiro, J. J. R. Fraústo da Silva, J. A. L. Silva, M. V. Kirillova, P. M. Reis, A. M. Kirillov, A. Palavra, Patent PT 103350, 2005; (e) A. J. L. Pombeiro, J. J. R. Fraústo da Silva, J. A. L. Silva, M. V. Kirillova, Patent PT 103352, 2005.

[3] (a) A. M. Kirillov, M. N. Kopylovich, M. V. Kirillova, M. Haukka, M. F. C. G. da Silva, A. J. L. Pombeiro, *Angew. Chem., Int. Ed.* 2005, 44, 4345; (b) A. M. Kirillov, M. N. Kopylovich, M. V. Kirillova, E. Yu. Karabach, M. Haukka, M. F. C. G. da Silva, A. J. L. Pombeiro, *Adv. Synth. Catal.* 2006, 348, 159; (c) D. S. Nesterov, V. N. Kokozay, V. V. Dyakonenko, O. V. Shishkin, J. Jezierska, A. Ozarowski, A. M. Kirillov, M. N. Kopylovich, A. J. L. Pombeiro, *Chem. Commun.* 2006, 4605.

[4] (a) A. J. L. Pombeiro, A. M. Kirillov, M. N. Kopylovich, M. V. Kirillova, M. Haukka, M. F. C. G. da Silva, Patent PT 103225, 2005; (b) A. J. L. Pombeiro, A. M. Kirillov, M. N. Kopylovich, V. N. Kokozay, D. S. Nesterov, Patent PT 103526, 2006.

[5] (a) *Ullmann's Encyclopedia of Industrial Chemistry; 6th* Edition, Wiley-VCH, Weinheim, 2002; (b) *Encyclopedia of Chemical Technology,* 5th Ed, Kirk-Othmer, Wiley, 2004.

[6] (a) C. Jia, T. Kitamura, Y. Fujiwara, *Acc. Chem. Res.* 2001, 34, 633. (b) Y. Fujiwara, K. Takaki, Y. Taniguchi, *Synlett* 1996, 591; (c) Y. Fujiwara, K. Takaki, Patent EP 0560656A2, 1993.

[7] A. T Bell, S. Mukhopadhyay, M. Zerella, J. G. Sunley, S. Gaemers, M. J. Muskett, U.S. Pat. No. 6,960,682, 2005.

[8] (a) M. Lin, A. Sen, J. Chem. *Soc., Chem. Commun.* 1992, 892; (b) A. Sen, M. Lin, U.S. Pat. No. 5,510,525, 1996; (c) A. Sen, M. Lin, U.S. Pat. No. 5,393,922, 1995.

[9] A. Shibamoto, S. Sakaguchi, Y. Ishii, *Tetrahedron Lett.* 2002, 43, 8859.

[10] (a) G. Suss-Fink, L. Gonzalez, G. B. Shul'pin, *Appl. Catal. A: Gen.* 2001, 217, 111; (b) G. V. Nizova, G. Suss-Fink, S. Stanislas, G. B. Shul'pin, *Chem. Commun.* 1998, 1885.

[11] (a) Sustainable Strategies for the *Upgrading of Natural Gas: Fundamentals, Challenges, and Opportunities*, E. G. Derouane, F. Parmon, F. Lemos, F. Ram(o)a Ribeiro (Eds.), NATO Science series, Vol. 191, Kluwer Academic Publ., Dordrecht, The Netherlands, 2005; (b) A. E. Shilov, G. B. Shul'pin, *Activation and Catalytic Reactions of Saturated Hydrocarbons in the Presence of Metal Complexes*, Kluwer Academic Publishers, Dordrecht, The Netherlands, 2000; (c) C. L. Hill, *Activation and Functionalization of Alkanes*, Wiley, New York, 1995.

[12] (a) R. E. Berry, E. M. Armstrong, R. L. Beddoes, D. Collison, S. N. Ertok, M. Helliwell, C. D. Garner, *Angew. Chem., Int. Ed.* 1999, 38, 795; (b) M. N. Kopylovich, A. M. Kirillov, A. K. Baev, A. J. L. Pombeiro, *J. Mol. Catal. A-Chem.* 2003, 206, 163.

The invention claimed is:

1. Method for the preparation of carboxylic acids comprising reacting, under mild conditions, an alkane with carbon monoxide and an oxidant, characterized by using, as reacting medium, an water/acetonitrile mixture in a volumetric ratio from 1.5:1 to 1:2, either in the absence or in the presence of a transition metal catalyst containing a ligand that coordinates through at least one nitrogen atom and one oxygen atom (N,O-ligand).

2. Method according to claim 1, characterized by the use, as alkane, of ethane, propane, n-butane, n-pentane, cyclopentane, n-hexane and cyclohexane, or a mixture comprising any of these alkanes, leading to the formation of the corresponding carboxylic acids with one further carbon atom, or to a mixture of the corresponding acids, respectively.

3. Method according to claim 1, characterized by the use, as oxidant, of a peroxodisulphate compound, used as such or in a mixture with another solid, liquid or gaseous oxidizing agent.

4. Method according to claim 3, characterized by the use, as peroxodisulphate compound, of potassium peroxodisulphate.

5. Method according to claim 1, characterized by the use, as catalyst, of a transition metal compound.

6. Method according to claim 5, characterized by the use, as transition metal compound, of the tetracopper triethanolaminate compound of formula $[O \subset Cu_4(N(CH_2CH_2O)_3)_4—(BOH)_4][BF_4]_2$.

7. Method according to claim 5, characterized by the use, as transition metal compound, of a compound selected from the group consisting of $[Cu_2(H_2tea)_2\{C_6H_4(COO)_2—1,4\}]_n—2nH_2O$, $[Cu(H_2tea)(N_3)]$, $Cu(NO_3)_2$-$2.5H_2O$, and $Ca[V\{ON(CH_2COO)_2\}_2]$, wherein $H_2$tea means monodeprotonated form of triethanolamine.

8. Method according to claim 1, characterized by the use of a reaction temperature in the 25-60° C. range and of a reaction time in the 2-6 h range.

9. Method according to claim 1, characterized by the optional use of recycled reactants, mixed solvent and catalyst.

10. Method according to claim 1, characterized by the control of the selectivity in the formation of carboxylic acid isomers by the type of catalyst and the relative amounts of alkane, CO and oxidant.

11. Method according to claim 2 wherein the corresponding carboxylic acid with one further carbon atom is closer from the group consisting of propionic, isobutyric, butyric, 2-methylbutanoic, 2-methylpentanoic, 2-ethylbutanoic, cyclopentanecarboxylic, 2-methylhexanoic, 2-ethylpentanoic and cyclohexanecarboxylic acids.

* * * * *